United States Patent [19]

Ettinger et al.

[11] Patent Number: 5,040,200

[45] Date of Patent: Aug. 13, 1991

[54] GAMMA-GAMMA RESONANCE IN ACTIVATION ANALYSIS, AND PARTICULARLY, ITS APPLICATION TO DETECTION OF NITROGEN BASED EXPLOSIVES IN LUGGAGE

[75] Inventors: Kamil V. Ettinger, Aberdeen, Scotland; Joseph H. Brondo, Jr., E. Hampton, N.Y.

[73] Assignee: Scientific Innovations, Inc., Wainscott, N.Y.

[21] Appl. No.: 349,326

[22] Filed: May 8, 1989

[51] Int. Cl.$^5$ .................. G01N 23/223; G01N 23/06; G01N 23/04; G01N 23/201
[52] U.S. Cl. ........................................ 378/88; 378/45; 378/53; 378/82; 378/86; 378/57; 378/49
[58] Field of Search ....................... 378/45, 49, 53, 70, 378/82, 83, 85, 86, 88, 116, 2, 50, 57, 63; 250/307, 303, 309, 390.04

[56] References Cited

U.S. PATENT DOCUMENTS

| | | |
|---|---|---|
| 3,171,961 | 3/1965 | Hule . |
| 3,255,352 | 6/1966 | Johnston . |
| 3,308,296 | 3/1967 | Cowan et al. . |
| 3,461,291 | 8/1969 | Goodman . |
| 3,654,464 | 4/1972 | Johnson, Jr. et al. . |
| 3,780,294 | 12/1973 | Sowerby . |
| 3,832,545 | 8/1974 | Bartko ............................ 250/390.04 |
| 3,997,787 | 12/1976 | Fearon et al. .................. 250/390.04 |
| 4,031,388 | 6/1977 | Morita et al. ......................... 378/45 |
| 4,314,155 | 2/1982 | Sowerby ............................... 378/88 |
| 4,327,290 | 4/1982 | Plasek . |
| 4,620,095 | 10/1986 | Miziolek . |
| 4,730,263 | 3/1988 | Mathis ................................. 378/70 |
| 4,756,866 | 7/1988 | Alvarez ............................. 376/157 |
| 4,760,252 | 7/1988 | Albats et al. . |
| 4,817,122 | 3/1989 | Badono et al. ....................... 378/88 |
| 4,851,687 | 7/1989 | Ettinger et al. ..................... 376/159 |
| 4,864,142 | 9/1989 | Gomberg ....................... 250/390.04 |
| 4,941,162 | 7/1990 | Vartsky et al. ...................... 375/57 |

OTHER PUBLICATIONS

Malanify et al.; "Nitrogen Isotopic . . . Protons"; (1974); 293–297.

Kurstedt, H. A., Jr. and Vantreace, Smart; "The Application of a Gamma-Ray Composition Measurement"; pp. 175–184; 1976.

Bodart, F. and Deconninck, G.; "Analysis of Selenium by Proton Bombardment"; pp. 171–181; 1972.

Primary Examiner—Edward P. Westin
Assistant Examiner—Don Wong
Attorney, Agent, or Firm—Scully, Scott, Murphy & Presser

[57] ABSTRACT

The invention relates to an apparatus and method for detecting the presence of an element of interest within an object. The object is positioned where a beam gamma rays of the required energy are directed to be scattered by the element of interest. The gamma rays are provided by excited atoms of the element of interest. The excited atoms result from the reaction of hydrogen or heavier ions and a suitable target. The excited atoms deexcite releasing gamma rays which are scattered by the element of interest within the object. The scattered gamma rays are detected, output signals are produced, processed and analyzed to determine the amount of the element of interest within the object. A preferred embodiment relates to the detection of nitrogen-based explosives in luggage.

24 Claims, 5 Drawing Sheets

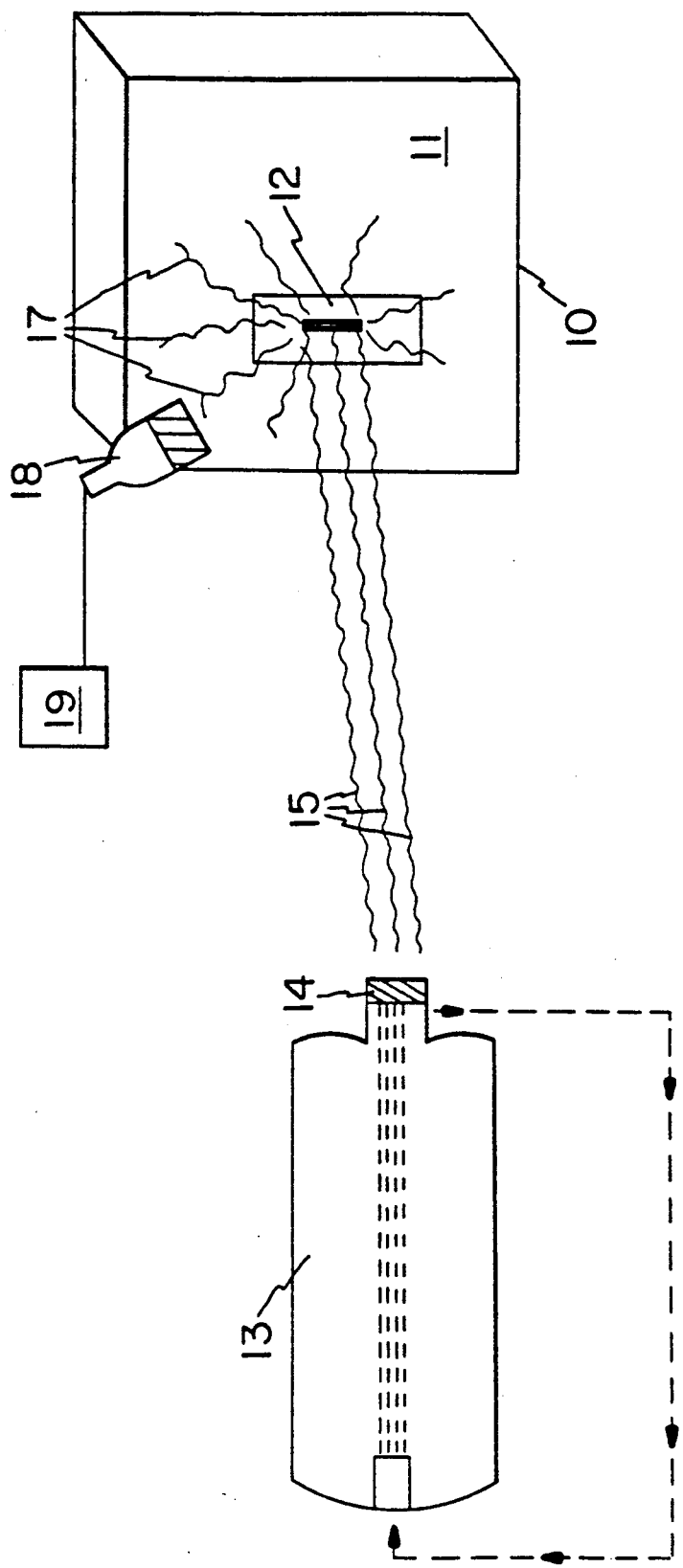

GAMMA-GAMMA RESONANCE IN ACTIVATION ANALYSIS, AND PARTICULARLY, ITS APPLICATION TO DETECTION OF NITROGEN BASED EXPLOSIVES IN LUGGAGE

BACKGROUND OF THE INVENTION

1. Field of the Invention

This invention is directed to an apparatus and method for scanning an object for an element of interest and especially for nitrogen in nitrogen-based explosives. More particularly, the invention is directed to an apparatus utilizing gamma-gamma resonance which causes gamma rays to be scattered by the element of interest that is detected and analyzed to provide a representation of the concentration of the element of interest contained within the object.

The subject apparatus and method finds further application in drug detection, body composition, industrial applications, substance detection, food analysis and medical applications including veterinary medicine.

2. Description of the Prior Art

The technique of nuclear resonance fluorescence has been employed for elemental and isotope analysis, both qualitative and quantitative. Particular applications include devices for well logging, borehole prospecting, on-stream analysis and the analysis of planet surfaces.

A significant threat to human life and property exists when an explosive device is concealed in luggage or parcels brought into building, aircraft, etc. As a result, there is a need by both the public and private sector of the country for a reliable technique for the detection of such explosive devices. As the threat of terrorist activities throughout the world, especially in airports, has increased the demand for an efficient and practical device for scanning luggage to determine the presence of explosives has intensified.

It is well known that explosives may be detected by sensing the amount of nitrogen in the object being examined. One technique of detecting nitrogen is by the subject method of nuclear resonance fluorescence (nuclear resonance scattering).

U.S. Pat. No. 3,171,961 relates to a method of well logging by nuclear resonance fluorescence for the detection of a given nucleus particularly carbon and oxygen. Nuclear reactions are described as a method of providing radiation wherein a bombarding nucleon from an accelerator is employed to produce an excited nucleus of the atoms being detected in a geological setting.

U.S. Pat. No. 2,726,838 relates to the use of the reaction between accelerated elementary charged particles and target means to provide a monoenergetic neutron source for bombarding the analyzed object thereby inducing a radioactive response which is detected. The preferred reaction is the reaction of deuterons with tritium.

U.S. Pat. No. 3,780,294 relates to the use of nuclear fluorescence for elemental analysis. The use of an accelerator to provide bombarding particles for nuclear reactions to produce gamma rays is discussed wherein the inventor indicates that the Doppler broadening may be too great and therefore would not provide a good method for the production of gamma rays.

SUMMARY OF THE INVENTION

The present invention is directed to an apparatus and method for scanning an object for an element of interest and determining the concentration of the element in the object. An accelerator provides hydrogen or heavier ions, preferably hydrogen or deuterium, directed at a target to produce excited atoms of the element of interest. The excited atoms deexcite to provide a beam of gamma rays of the required energy. The object is positioned within the beam of gamma rays. The gamma rays are scattered by the element of interest within the object. The resonantly scattered gamma rays are then detected and output signals produced. The output signals are representative of the amount and energy of the gamma rays thereby allowing determination of the presence and amount of the element of interest within the object being scanned.

The apparatus and method are applied to a variety of objects for analysis thereof. The detection of nitrogen in explosives represents a preferred embodiment of the subject invention. Further embodiments include the detection of drugs in an object, body composition determination, industrial applications, substance detection, food analysis and medical and veterinary examination.

BRIEF DESCRIPTION OF THE DRAWINGS

FIG. 1 is a schematic illustration of the apparatus for detecting the presence of an element of interest in accordance with the present invention.

DETAILED DESCRIPTION OF THE INVENTION

Figure 2A:
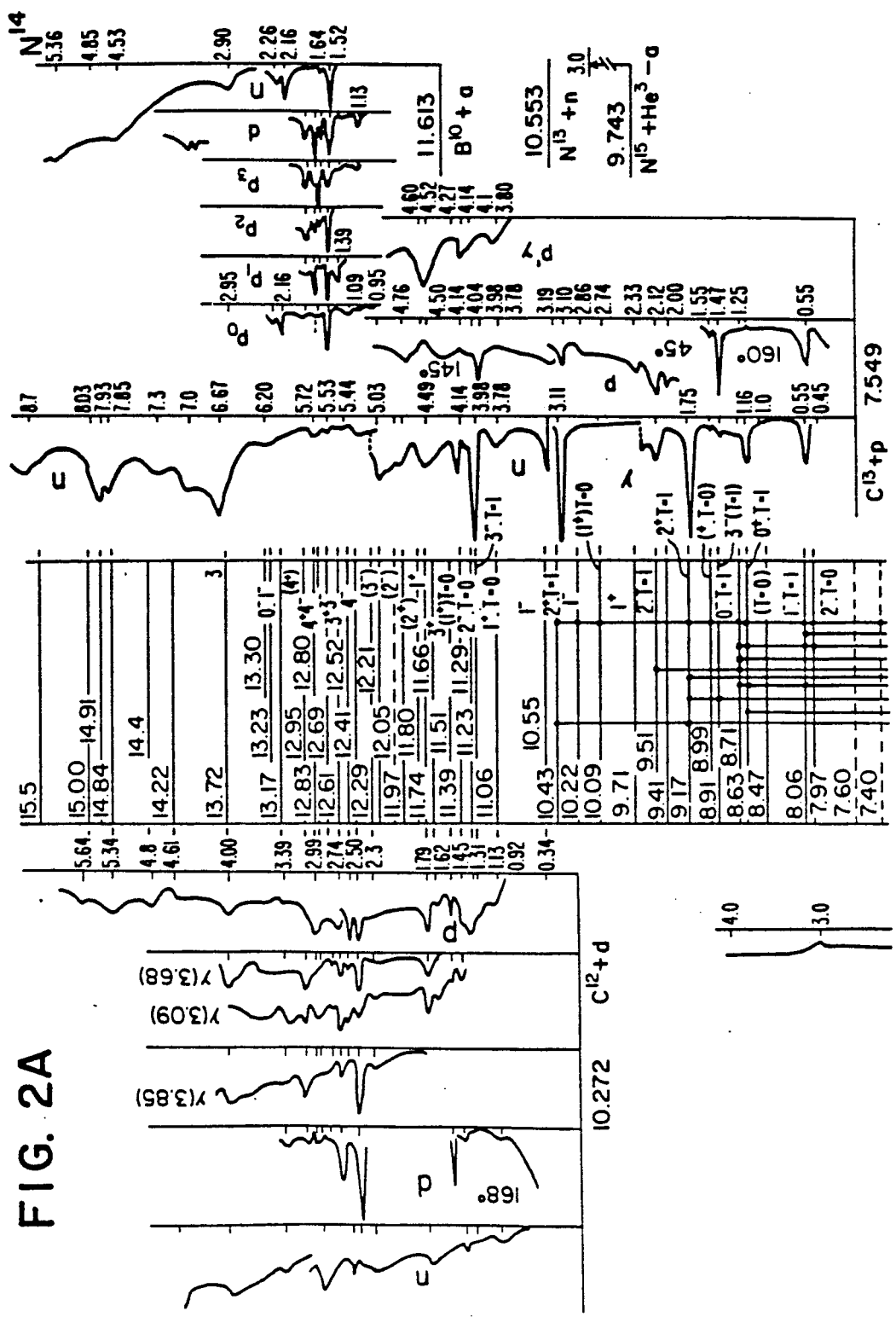
FIG. 2 is a nuclear resonance scheme of charged particle resonances for N-14.

The gamma-gamma resonance method is an application of the phenomenon known as Nuclear Resonance Scattering or Nuclear Resonance Fluorescence. In this technique the gamma radiation of properly and precisely chosen energy is used to excite the corresponding energy levels in the analyzed object which plays the role of the scatterer. The resonantly scattered radiation is then detected and analyzed.

The phenomenon of nuclear resonant fluorescence is a particular case of elastic scattering of photons from nuclei, with the photon energy and the energy of the nuclear level exactly matching one another. This process, which is characterized by a very large cross section in comparison with other photon scattering processes has been used almost exclusively for the determination of nuclear lifetimes and has been applied to the activation analysis of minerals and the determination of the concentration of some elements in vivo in man. In the activation analysis applications, the nuclear resonance scattering has been used as a method of excitation of nuclear levels in analyzed objects.

A gamma ray emitted by a nucleus initially at rest has an energy only approximately equal to the difference between the energy levels involved in the radiative transition. In fact, the emitted quantum is lacking the amount of energy taken by the recoiling nucleus.

Photons are characterized by their energy $E_\gamma$ and their momentum $P_\gamma$, which are related through $$P_\gamma = E_\gamma/c \qquad (1)$$

where c is the velocity of light.

Thus, if an excited nucleus, initially at rest but free to recoil in the laboratory frame, deexcites by emission of a gamma ray, the conservation of momentum requires that this nucleus should recoil in the direction opposite to that of the photon.

The recoil velocity V is determined by the momentum conservation:

$$MV = -E_\gamma/c \quad (2)$$

where M is the mass of nucleus.

The energy balance gives:

$$E = MV^2/2 + E_\gamma \quad (3)$$

where E is the energy of the radiative transition. It can be also written as:

$$E = E_\gamma + E_\gamma^2/2Mc^2 \quad (4)$$

The energy of the emitted gamma ray is thus slightly less than the transition energy, the difference, expressed in practical units, is:

$$E - E_\gamma = (5.37 \times 10^{-4})E_\gamma^2/A \text{ [in MeV]} \quad (5)$$

where A is the atomic number of the emitting nucleus. Since E is not very different from $E_\gamma$, the following approximation can be made:

$$E - E_\gamma = (5.37 \times 10^{-4})E^2/A \quad (6)$$

A similar phenomenon is observed in gamma ray absorption i.e. the same amount of energy is transferred to the recoiling nucleus. The photon energy which is necessary to excite a transition E is:

$$E_\gamma = E + E^2/2Mc^2 \quad (7)$$

Consequently the photon corresponding to the transition energy E is off resonance by an amount $E^2/Mc^2$ In other words, the nucleus is not capable of absorbing its own radiation if the difference of both recoils, i.e. at the moment of emission and at the moment of absorption, is not compensated in some way.

When a gamma ray is emitted by a nucleus which is moving with respect to the detector or scatterer, a small energy shift is observed. This effect is called the Doppler effect in analogy with the equivalent phenomenon observed in acoustics. If v is the nucleus velocity before the act of emission, we have the relationship:

$$E_\gamma = E'_\gamma[1 + (v/c)\cos\theta] \quad (8)$$

where $\theta$ is the angle between the direction of recoil and the direction of gamma quantum. The use of Doppler effect has been the principal method of compensation of energy disparity between the photon and appropriate nuclear level. It has been employed in the form of imparting motion of emitters and scatterers in respect of each other by direct mechanical motion, by heating of the emitter or absorber or by employing recoil of the parent nucleus in processes of beta decay briefly preceding the emission of gamma ray photon. A similar Doppler energy compensation can be attained by means of nuclear collisions in which the exciting photons are generated.

The energy deficit arising from the recoil associated with absorption can be compensated by exciting the primary emitters with fast charged particles through the process of inelastic scattering. In this process the nucleus acquires some of the kinetic energy of the incoming projectile and the degree of compensation depends upon the angle between the movement of the struck nucleus and the direction in which the quantum from deexcitation is emitted.

Similarly, it is possible to obtain the compensating shift in gamma ray energy in neutron capture processes. It is known that when epithermal neutrons are captured into very short lived, energetically broadened states, the energies of some of the emitted gamma rays are slightly higher than those appearing in the thermal neutron capture spectra. Neutron capture of a non-zero energy neutron is also a non elastic collision, and, thus in addition, the capturing nucleus exhibits a recoil, because of the need to preserve the momentum.

The method of resonant scattering (NRF) has been used in the past in activation analysis, but the method of producing the exciting radiation represents a novelty. This method is based on exploitation of the phenomenon of charged particle resonance, a different resonance effect in nucleus from the above described resonant scattering of gamma quanta.

The usual nuclear reaction is characterized by the interaction of the incident particle with a stationary target nucleus, neglecting the thermal motion of the latter. As a consequence of the interaction a nuclear reaction may take place, and the incident particle may be scattered, captured, disintegrated (stripped) or may be aggrandized by picking up a nucleon from the target. The target nucleus, apart from a recoil, may be excited, whether transformed into another species or not. Resonance takes place when the system composed of incident particle and the target nucleus has energy equal to the energy level of the compound nucleus formed. Excited nucleus, may stay in the metastable state for a considerable time, or may deexcite almost instantaneously with an emission of gamma quanta or other particles. In fact, there may be more than one mode of decay from the excited state. The cross sections for these reactions are a function of energy, and in general can be classified as resonant or non-resonant, with the borderline between these two types diffuse and uncertain. Examples of non-resonant reactions are Coulomb and potential scattering and so called direct reactions, like stripping (Oppenheimer-Phillips reaction is a special case of these) or pick up. The term 'resonant reactions' is used for processes in which the cross section exhibits pronounced maxima and minima as the energy of the incident particle is varied. From the point of view of their proposed use in activation analysis, the important numerical parameters of resonant reaction, called sometimes, simply, resonances are energy of the projectile, energies of excited levels, energies of emitted gamma rays or charged particles, cross section at the peak of the resonance (barns) or an integral of cross sections taken over the area of resonance (barns$\times$eV) and the resonance width (eV).

The scanning apparatus of the present invention is schematically illustrated in FIG. 1 in a preferred embodiment for scanning luggage. The apparatus generally includes a housing 10 having a cavity 11 for receiving an object 12 to be scanned. The housing may include a means for transporting the object 12 through the cavity 11. Accelerator 13 provides hydrogen or heavier ions, preferably hydrogen or deuterium ions, directed at a target 14 to provide excited atoms of the element of interest which deexcite and thereby produce primary gamma rays 15 of the required energy to be resonantly scattered by the element of interest 16 within the cavity 11. The resonantly scattered gamma rays 17 are observed by detector 18 which produce output signals representative of the energy of the gamma rays 17. Means 19 processes and analyzes the output signals for determining the amount of the element of interest. Detector 18 observes the resonantly scattered gamma rays 17 preferably at an angle of 45° to 175°, most preferably larger than 90 degrees from the axis of bombardment at which the primary gamma rays 15 interact with the object 12 being scanned.

The incident particle interacts with the target nucleus to form a compound nucleus. The energy of the compound nucleus, neglecting the recoil, is equal to the sum of the binding energy of the projectile within the target plus the kinetic energy in the center of the mass of the projectile. If this excitation energy corresponds to one of the energy levels of the compound nucleus, the resonance takes place and the corresponding cross section shows a maximum. The intensity of gamma rays arising from the deexcitation reaches a maximum. Examples of such charged particle resonances are the reactions C-13 (p,gamma) N-14 at an energy of 1747.6 keV and C-12 (d, gamma) N-14 at an energy of approximately 2500 keV. The (p,gamma) reactions were tabulated in J. W. Butler, Report of the Naval Research Laboratory, NRL-5282 (1959). More recent data on charged particle resonances can be found in Nuclear Data Sheets and also in the compilations of nuclear energy levels published regularly by Endt and Ajzenberg-Selove in Nuclear Physics ser.A.

Figure 2B:
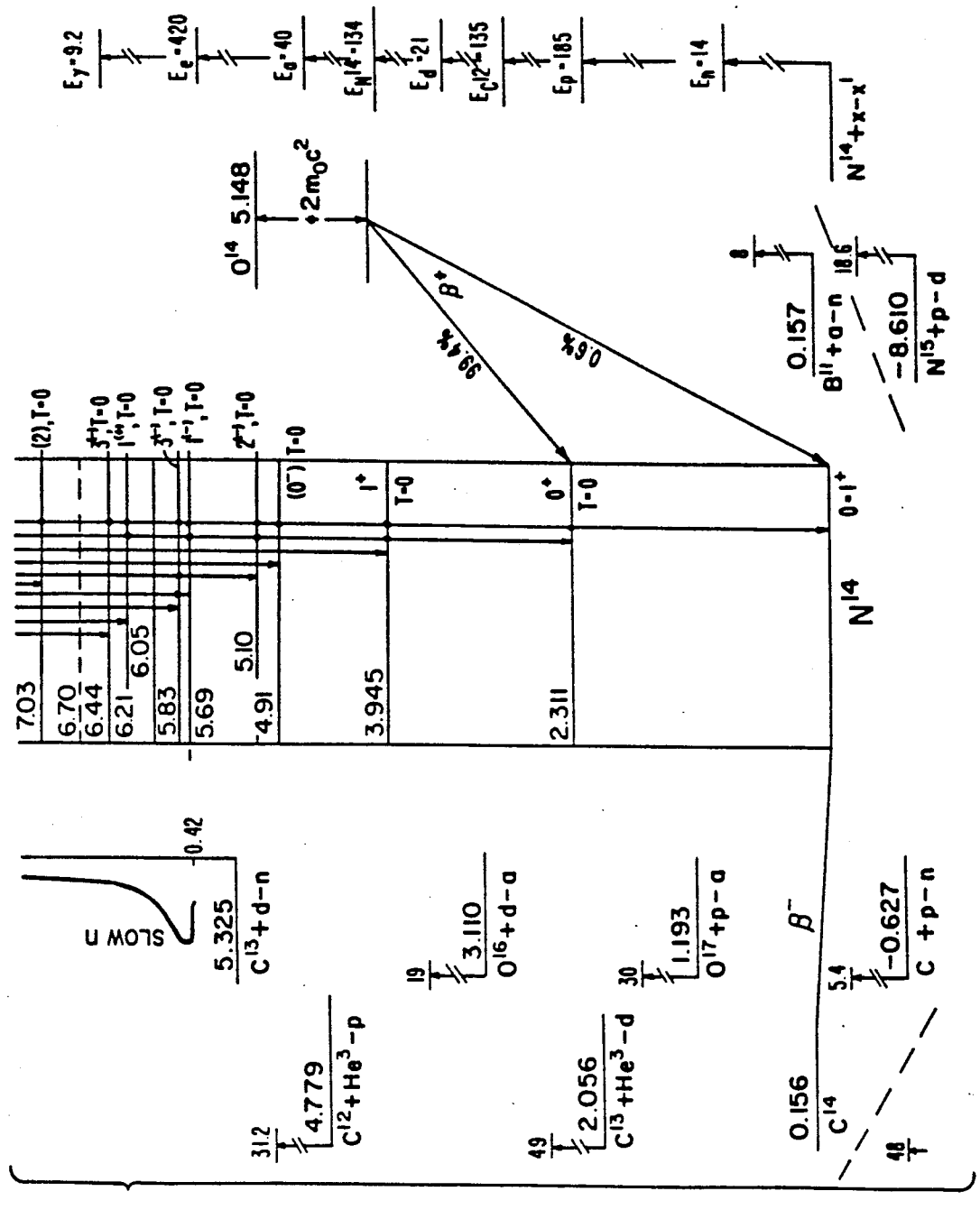

An example of nuclear level scheme with an indication of charged particle resonance for N-14 from Nuclear Data Tables is shown in FIG. 2. The value of 7.549 MeV corresponds to the binding energy of a proton in the nucleus of C-13 and 10.272 MeV corresponds to the binding energy of a deuteron in the nucleus of C-12, as it was known at the time of publication. The vertical lines show an approximate shape of the dependence of the reaction cross section upon the energy of proton or deuteron projectile. The gamma transitions take place between the levels of final nucleus and their intensities depending upon the probabilities of various transitions. The resonances at 1747 keV and 550 keV for C-13+p and the resonance at approximately 2500 keV for C-12+d are clearly recognizable.

The gamma rays emitted in these resonances can be used for excitation of the scatterer (analyzed object) in the activation analysis technique. These gamma rays include transitions to the ground state, unless specifically barred by the selection rules, and thus correspond approximately to the energy levels in the scatterer. The recoil compensation can be provided by the selection of the angle at which the gamma rays are observed with respect to the charged particle beam and, if necessary, the target can be provided in a gaseous form, to take advantage of the 'in-flight' Doppler shift.

While most of the attention is on the three principal elements of organic matter, the technique of gamma-gamma excitation is, however, fairly general and any of the resonances can be used with an appropriate selection of the target, projectile and bombarding particle energy. The only elements which cannot be excited by this method are hydrogen and helium. It should however be kept in mind that with an increase in the atomic number of the target element the energy of the projectiles must be increased so that they can penetrate the Coulomb barrier.

The main requirements for the charged particle source are stability of the energy of projectiles striking the target and sufficient intensity of the beam to provide an adequate photon flux, which in turns depends upon the cross sections of the reaction in use. The energy stability should be such that instabilities do not cause significant fluctuations in the intensity of the photon flux.

If the analysis is to be preformed for more than one element, the accelerator should have an electronic voltage adjustment and control and the beam should be able to strike different targets. This function of target switching can be done either mechanically or by a deflection device for the beam operated electrostatically or magnetically.

The type of the accelerator is dictated only by the operational and financial imperatives. Electrostatic and Radio Frequency Quadrupole accelerators are the most obvious types.

All the existent gamma- and X-ray radiation detectors are, so far, wide band devices i.e. responsive to the quanta in a broad range of energies limited by the absorption of the detector window on the low energy side and the decreasing detection efficiency on the other, high energy side. This is because the detection of photons is a consequence of their interaction with atomic electrons and, thus, requires only an energy of the order of tens of electron volts to be released inside the detector sensitive volume.

On the other hand, nuclear resonance fluorescence is a nuclear process and requires energies of much higher order, frequently more than 10 MeV. Because of the resonant nature of interaction, and particularly, because of very narrow width of resonances involved, the nuclear resonance fluorescence offers a possibility of narrowing the response of radiation detectors to very narrow energy bandwidths i.e. an energy filtration.

Figure 3:
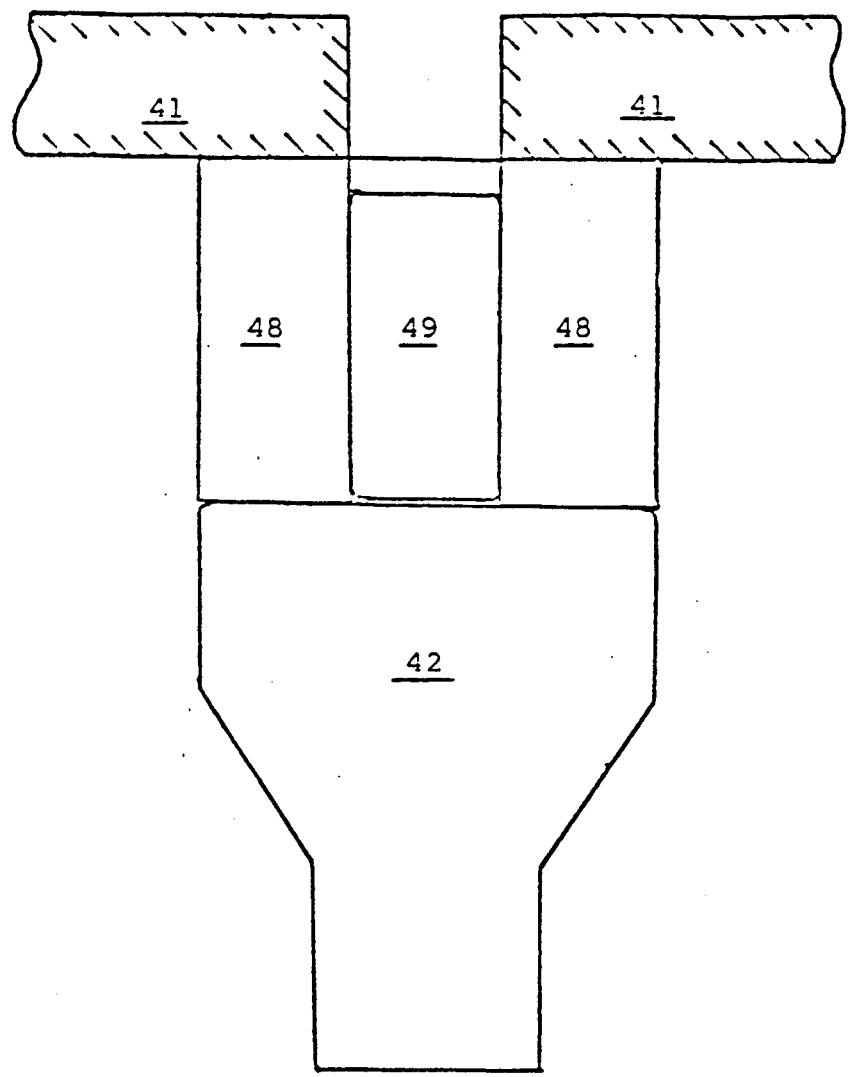
FIG. 3 is a schematic illustration of passive nuclear resonance fluorescence detection in accordance with the present invention.

This effect can be achieved by incorporating the nuclear resonance fluorescence filtering element into the detector system. The nuclear resonance fluorescence element can be either passive or active. In the passive NRF system the gamma ray flux 35 from the source i.e. the analyzed object 32 cannot reach the detector 38 directly but only after scattering from the resonance scatterer 39 as in FIG. 3. The analyzed object 32 is exposed to neutron flux of suitably chosen energy so that gamma ray photons 37 emitted by the analyzed object 32 contain the quanta of energy required to cause resonant absorption, as given by eq.(7). If neutron capture in the object takes place in nuclei with atomic mass A, the resonance scatterer should contain nuclei of a heavier isotope with atomic mass (Z+1). This is a consequence of fact that following the capture of a neutron by a nucleus of mass Z, the subsequent emission of gamma quantum takes place from an isotope of mass (Z+1). If, on the other hand, the nuclei in the object are excited in the process of inelastic scattering, the atomic mass does not change. In such a case the same nuclide should be present in the resonance scatterer 39 as the one present in the analyzed object 32.

In the more general case one can envisage inelastic scattering of heavy particles other than neutrons. Gamma rays from such scattering process in the object can be similarly resonantly scattered by nuclei of the same nuclide in the NRF scatterer, provided the Doppler compensation of energy is satisfactory. For capture of other particles than neutrons in the object containing nuclei M, the resulting nucleus is N $$^{A}_{Z}M + ^{B}_{Y}P = ^{A+B}_{Z+Y}N \qquad (9)$$

where $$^{B}_{Y}P$$

is the projectile.

In a particular case of pick-up reactions with deuterons (Oppenheimer-Phillips reaction) or $^3$He, the nucleus retains a neutron from the charged projectile. In this case where the object contains nuclei with atomic mass Z, the NRF scatterer should contain the isotope with a mass (Z+1), as in the case of simple neutron capture.

Figure 4:
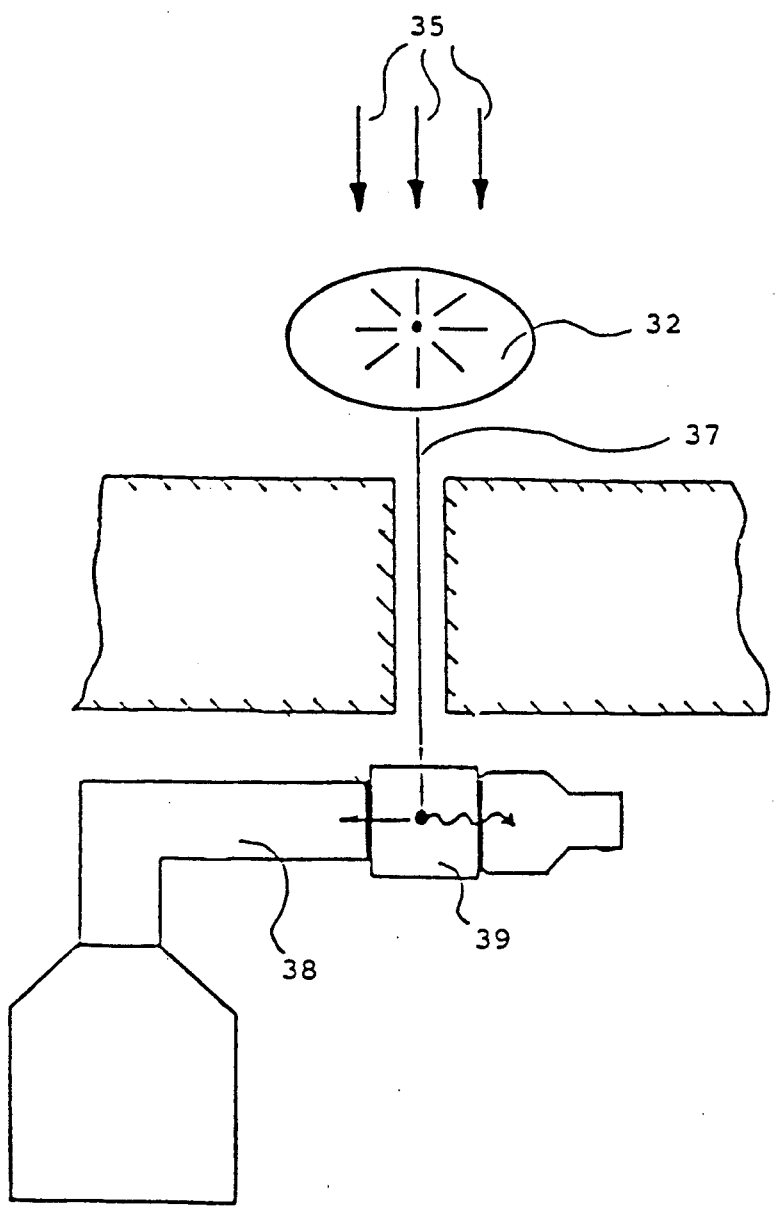
FIG. 4 is a schematic illustration of active nuclear resonance fluorescence detection in accordance with the present invention.

If the NRF scatterer provides an indication that scattering has taken place, then it operates in an active mode. An example of an active mode is shown in FIG. 4 wherein resonant scattering nuclei are incorporated into the scintillator or into the gas, liquid or solid phase of a sufficiently sensitive radiation detector. E.g. for the detection of nitrogen ($14_N$) one would incorporate into the scintillator or active volume of the ionization based detector, nuclei of $15_N$, if the gamma rays are produced in the analyzed object by neutron capture, or $14_N$ if gamma rays originate in inelastic collisions. If nuclear scattering takes place within the scintillator or the active volume of the ionization detector, the recoiling nucleus produces a short track in the scintillator or ionization burst in the ionization detector. The energy of recoil is given by eq. (6), and for most practical cases is of an order of few keV. Such a recoil can be detected in a purpose designed detector and, originating from a heavy nuclei, may be discriminated against the electron background by one of known techniques, e.g. by rise time analysis. The electron background is produced in Compton scattering interactions.

In addition to rise time discrimination, an energy discrimination of detected recoils may provide an identification of an elastic event. Only if the pulse from the detector fits into an energy window corresponding to a recoil in the active NRF scatterer, and its rise time is within time interval proper for the heavy recoiling nucleus, it could be assumed that a 'resonant' photon has been scattered into the main detector. The proper selection of events is achieved by employing a coincidence between the recoil pulse from the active NRF scatterer and the pulse from the main detector as shown in FIG. 4.

There is no limitation of what is the design and composition of the main detector. Particularly, scintillation detector, proportional counters, solid state detectors, multiwire proportional chambers are suitable for this application. The only requirement is that the rise time of the pulse produced by radiation in the main detector is sufficiently short to enable its use as one of the inputs to a coincidence circuit.

In some applications it may be desirable to use the same photomultiplier 42 for both active NRF scatterer and for the main gamma ray detector as shown in FIG. 4. The identification of events involving formation of a recoil track followed by detection of gamma quantum in the main detector can be achieved by means of a pulse shape analyzer which will permit to identify separately both components of the light pulse. This can be done if the time constants of light pulses in both detectors (i.e. in the active NRF scatterer and in the main detector) are significantly different, as in the case of plastic or liquid scintillator and an inorganic crystal.

The role of energy selector at the present state of radiation detector technology is played by pulse amplitude discriminators, either in their simple forms or in a form of a multichannel analyzer. In the the multichannel analyzer the rate limiting step is analog-to-digital conversion. The effect of energy filtering is to reduce the counting rate before the conversion takes place. This reduction is a consequence of an introduction of an additional scattering stage in form of the active NRF scatterer into the process of detection. This process of scattering will much more profoundly affect the intensity of gamma rays detected off resonance than within the resonance. The filtration ratio, defined as an attenuation ratio of gamma ray intensity at resonance energy to that off resonance, can be as high as 500-1000 times, for energies of gamma rays and nuclei levels perfectly matched. However, such match may be difficult to achieve and much lower filtration ratios are expected in practice.

An important feature of energy filtration of gamma rays in detection systems by means of Nuclear Resonance Fluorescence is that the filtration can be achieved for more than one level per nuclide, at the same time and in the same set up. For nuclides exhibiting multiple transitions and particularly closely spaced on energy scale transitions the filtration cannot be practically achieved by solely electronic means. Furthermore, the use of filtration by means of Nuclear Resonance Fluorescence can deal with many nuclides at the same time in the analyzed object. What is needed, is incorporation of appropriate nuclides into the NRF scatterer. There is no low energy limit for passive filtration, but for an active filtration system the limit is set by the noise and background level in the active NRF scatterer detector. When, owing to this noise, the NRF scatterer detector can no longer furnish a reliable input to the coincidence system, the system may still be used in the same geometrical configuration as a passive system, with the consequent degradation of the degree of filtration. With an increasing atomic mass of the scatterer the energy of recoil is reduced and, again, the availability of sufficiently reliable, input to the coincidence circuit limits application of active NRF filtering. The passive fileratjng remains unaffected.

For the detection of nitrogen-based explosives in luggage as shown in FIG. 1 the collimated beam from the accelerator is directed at the piece of luggage. The resonantly scattered radiation is observed at an angle of scattering larger than 90 degrees or, at least, equal, by means of energy selective radiation detectors e.g. Ge(Li) or HPGe. The simultaneous observation of resonant and non-resonant scattering (by observing the intensity of scattered beam at the resonance peak and off) permits detection of the presence of the sought element, by measuring and, if desirable, displaying e.g. the ratio of resonant to non-resonant signal. The intensity fluctuations in the beam must be considered when displaying the ratio.

The scanning of objects of luggage will preferably be performed by a mechanical motion of the piece in respect of a stationary target and detector system. However, in principle it is possible to design a system in which the scanning is provided by non-mechanical displacement of the gamma illuminating beam spot on the surface of the luggage. In the scanning mode the resolution of the image depends upon the size of the beam. The scanning is, obviously, not limited to the checking of baggage, but can be used for industrial, medical and investigation of art purposes.

The main advantage of the gamma-gamma system is that it does not induce radioactivity in the checked object as a result of resonant gamma-gamma scattering. The luggage after checking can be immediately taken away by a passenger or luggage carrier. The principle of the method permits the use of most light and medium-heavy elements in the determination of different nuclides.

In addition to inspection for the detection of explosives, luggage can be inspected for the detection of drugs which may be contained therein. In this embodiment a ratio of different elements is employed thereby indicative of the presence of the drug of interest. Body composition may also be determined for applications in both medical and veterinary medicine. Quality control of food is accomplished by detection of the elements and also the ratio of elements contained in said food.

While illustrative embodiments of the subject invention have been described and illustrated, it is obvious that various changes and modifications can be made therein without departing from the spirit of the present invention which should be limited only by the scope of the appended claims.

We claim:

1. An apparatus for scanning an object to determine the concentration of at least one element of interest in the object comprising:
   means for producing primary gamma rays of required energy to be resonantly scattered by at least one element to be detected, said means for producing gamma rays includes an accelerator providing hydrogen or heavier ions directed at a predetermined target to thereby producing excited atoms of the at least one element of interest which deexcite and provide a beam of said primary gamma rays of the required energy to be resonantly scattered by the at least one element of interest;
   means for positioning said object within the beam of gamma rays;
   means for detecting the resonantly scattered gamma rays and for producing output signals representative of the energy of said resonantly scattered gamma rays; and
   means for processing and analyzing said output signal for determining the amount of the at least one element of interest.

2. The apparatus of claim 1 wherein said at least one element of interest is $^{14}N$.

3. The apparatus of claim 2 wherein said accelerator provides hydrogen ions and said target is $^{13}C$.

4. The apparatus of claim 2 wherein said accelerator provides deuterium ions and said target is $^{12}C$.

5. The apparatus of claims 1, 3 or 4 wherein said means for detecting the scattered gamma rays is positioned at an angle greater than 90 degrees from the axis of bombardment at which the primary gamma rays interact with the object.

6. The apparatus of claim 1 wherein said means for detecting the scattered gamma rays includes a liquid scintillator and high resolution detector.

7. The apparatus of claim 6 wherein the liquid scintillator and high resolution detector is a Ge(Li) or HPGe detector.

8. The apparatus of claim 1 wherein the accelerator is an electrostatic accelerator or a radio frequency quadrapole accelerator.

9. The apparatus of claim 1 wherein the means for positioning includes means for transporting the object through the beam of gamma rays.

10. The apparatus of claim 9 wherein said means for positioning includes a conveyor means for introducing said object to be scanned into said means for transporting said object through said beam of gamma rays.

11. The apparatus of claim 1 for scanning an object to determine the presence and concentration of two or more elements of interest in said object wherein said accelerator includes an electronic voltage adjustment and a control beam for striking two or more targets.

12. The apparatus of claim 11 wherein said two or more element of interest includes a first and second elements of interest within a drug and said means for producing primary gamma rays includes a first and second means for producing primary gamma rays of the required energy to be resonantly scattered by the first and second element to be detected.

13. The apparatus of claim 1 wherein the means for detecting the scattered gamma rays includes an energy filtering element.

14. The apparatus of claim 13 wherein the energy filtering element is in a passive mode.

15. The apparatus of claim 13 wherein the energy filtering element is in an active mode.

16. The apparatus of claim 1 wherein the detecting means is selected from the group consisting of scintillation detector, proportional counter, solid state detector, and multiwire proportional chamber.

17. The apparatus of claim 5 which further includes
   means for detecting the non-resonantly scattered gamma rays and for producing output signals representative of the energy of the non-resonantly scattered gamma rays;
   means for processing and analyzing said non-resonant output signals; and
   means for generating a ratio of resonant to non-resonant output signals.

18. The apparatus of claim 17 wherein said means for generating a ratio includes a means of displaying said ratio.

19. A method of scanning an object for an element of interest in the object, comprising:
   accelerating hydrogen or heavier ions directed toward a target to produce excited atoms of the element of interest, said excited atoms deexciting to provide a beam primary gamma rays of the required energy to be resonantly scattered by the element of interest within the object; said primary gamma rays directed toward the object;
   positioning said object within said beam of primary gamma rays;
   detecting the resonantly scattered gamma rays and producing output signals representative of the energy of said gamma rays; and
   analyzing said output signals to determine the concentration of the element of interest.

20. A method of scanning an object for nitrogen in the object, comprising:
   accelerating hydrogen or deuterium ions directed toward $^{12}C$ or $^{13}C$ to produce excited atoms of nitrogen, said excited atoms deexciting to provide primary gamma rays of the required energy to be resonantly scattered by the nitrogen within the object; said primary gamma rays directed toward the object;

positioning said object within said beam of gamma rays;

detecting the resonantly scattered gamma rays and producing output signals representative of the energy of said gamma rays; and analyzing said output signals to determine the concentration of the nitrogen.

21. The method of claims 19 or 20 which further includes detecting the non-resonantly scattered gamma rays and producing output signals representative of the energy of the non-resonantly scattered gamma rays;

processing and analyzing said non-resonant output signals; and generating a ratio of resonant to non-resonant output signals.

22. The method of claim 21 wherein generating a ratio includes displaying said ratio.

23. A method of scanning an object for a drug of interest within said object, comprising accelerating hydrogen or heavier ions directed toward a target to produce excited atoms of an element within the drug of interest, said excited atoms deexciting to provide a beam of primary gamma rays of the element; said beam of primary gamma rays directed toward the object;

positioning said object within said beam of primary gamma rays;

detecting the resonantly scattered gamma rays and producing output signals representative of the energy of said resonantly scattered gamma rays; and analyzing said output signals to determine the concentration of the element within the object.

24. The method of claim 23 which further includes accelerating hydrogen or heavier ions toward two targets to produce excited atoms of two elements within the drug of interest to provide two primary gamma rays of the two elements; and analyzing said output signals to determine the ratio of the concentration of the two elements within the object.

* * * * *